US00PP15154P2

(12) United States Plant Patent
Scorza et al.

(10) Patent No.: US PP15,154 P2
(45) Date of Patent: Sep. 21, 2004

(54) PLUM TREE NAMED 'HONEYSWEET'

(50) Latin Name: *Prunus domestica L.*
Varietal Denomination: HoneySweet

(75) Inventors: Ralph Scorza, Shepherdstown, WV (US); Michel Ravelonandro, Villenave d'Ornon (FR); Dennis Gonsalves, Hilo, HI (US)

(73) Assignees: The United States of America as represented by the Secretary of Agriculture, Washington, DC (US); Institut National de la Recherche Agronomique, Paris Cedex (FR); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/942,866

(22) Filed: Aug. 31, 2001

(51) Int. Cl.[7] ..... A01H 5/00
(52) U.S. Cl. ..... Plt./184
(58) Field of Search ..... Plt./184

(56) References Cited

PUBLICATIONS

Scorza et al., "Transgenic Plums (*Prunus domestica* L) Express the Plum Pox Virus Protein Gene", Plant Cell Reports, vol. 14, pp 18–22, 1994.*
Scorza, R., "Significant Resitance of Transgenic Plums Against the Four Serotypes of Plum Pox Potyvirus", *Acta Hort.*, vol. 550, pp. 431–435, ISHS 2001.
Scorza, R., "Transgenic Plums Resistant to Plum Pox Virus Infection and Preliminary Results of Cross–Hybridization", *Acta Hort.*, vol. 478, pp. 67–71, ISHS 1998.
Ravelonandro, M., et al., "Resistance of Transgenic *Prunus domestica* to Plum Pox Virus Infection", *Plant Disease*, vol. 81, pp. 1231–1235, Nov. 1997.
Scorza, R., et al., "Post–transcriptional Gene Silencing in Plum Pox Virus Resistant Transgenic European Plum Containing the Plum Pox Potyvirus Coat Protein Gene", *Transgenic Research*, vol. 10, pp. 201–209, 2001.
Scorza, R., et al., Transferring Potyvirus Coat Protein Genes Through Hybridization of Transgenic Plants to Produce Plum Pox Virus Resistant Plums (*Prunus Domestica* L.) *Acta Hort.*, vol. 472, pp. 421–427, ISHS 1998.
Scorza, R., et al., "Transgenic Plums (*Prunus domestica* L.) Express the Plum Pox Virus Coat Protein Gene", *Plant Cell Reports*, vol. 14, pp. 18–22, 1994.

* cited by examiner

*Primary Examiner*—Anne Marie Grunberg
(74) *Attorney, Agent, or Firm*—John D. Fado; Evelyn M. Rabin

(57) ABSTRACT

A new and distinct variety of plum is transgenic and is characterized by the presence of the plum pox virus coat protein gene and genes for kanamycin resistance (NPTII) and β-glucuronidase (GUS). The plum pox virus coat protein transgene imparts a high level of resistance to plum pox virus. In field tests, 'HoneySweet' has been shown to be immune to transmission of plum pox virus by the natural aphid vectors present at the field test site. When 'HoneySweet' is bud-graft inoculated with plum pox virus, it supports only a very low level of virus and is symptomless or shows only transient, very mild symptoms. Fruit of 'HoneySweet' is large and sweet, firm and attractive. The tree is productive vigorous, with an upright growth habit.

2 Drawing Sheets

BACKGROUND OF THE NEW VARIETY

The present invention relates to a new and distinct variety of plum tree (*Prunus domestica* L.) which is named 'HoneySweet', in particular to a plum tree having the plum pox virus (PPV) coat protein gene which imparts a high level of resistance to infection by PPV.

The new variety is especially attractive commercially due to its PPV resistance. Plum pox virus is the most serious virus disease of plum and other Prunus species and has spread throughout Europe and England and has been reported in India, Egypt and Chile. More recently, outbreaks of the disease have been reported in the eastern United States and Canada. Plum pox virus causes serious fruit loss and can cause tree death. In the Czech Republic alone, the number of plum trees has dropped from a high of 18 million to less than 5 million due to the presence of PPV in the orchards. Thus a tree having resistance to infection by the virus would be a highly desirable commercial product in the U.S.

The new variety was originated in vitro by *Agrobacterium tumafaciens*-mediated transformation of open pollinated seed of the 'Bluebyrd' (not patented) plum with the PPV coat protein gene at the Appalachian Fruit Research Station, Agricultural Research Service, U.S. Department of Agriculture in Kearneysville, W. Va. Transformation of hypocotyl slices from an open pollinated seed of 'Bluebyrd' was carried out, and transgenic plants containing the PPV coat protein gene were successfully generated from the hypocotyl slices. In addition to the PPV coat protein gene, the plants also contained genes for kanamycin resistance (NPTII) and β-glucuronidase (GUS), transformation selection markers. The transformation and regeneration process is described in detail in Scorza et al. (1994. *Plant Cell Reports.* vol. 14, pp. 18–22).

The new variety was selected from a group of 21 clones derived from the transformation of hypocotyl slices from open pollinated seed of the 'Bluebyrd' plum. The new variety was distinct from the remaining transgenic clones containing the PPV coat protein, NPTII and GUS genes due to the presence of multiple copies of the PPV coat protein transgene, the low amount of PPV coat protein RNA produced and the absence of detectable PPV coat protein (Scorza et al., supra). Resistance is mediated through post transcriptional gene silencing (as described in Scorza et al. 2001. *Transgenic Research.* vol. 10, pp. 201–209).

While the female (seed) parent of 'HoneySweet' is 'Bluebyrd', the pollen source (male parent) is unknown. The new variety is distinct from its seed parent by its fruit quality, earlier ripening date (about 1 week earlier) and by the presence of the PPV coat protein, NPTII and GUS transgenes and by its high level of resistance to PPV. Since, at the time of the invention, no other plum tree contained these genes either singly or jointly, the pollen parent could not have contributed any of them, thus the new variety is also distinct from its pollen parent. Plum pox virus resistance is described in Ravelonandro et al. (1997. *Plant Disease.* vol. 81, pp. 1231–1235).

The new variety was originally selected in vitro as a regenerated shoot from a 'Bluebyrd' plum seed hypocotyl slice that had been transfected with *Agrobacterium tumefaciens* EHA 101 carrying the plasmid pGA482GG/PPV-CP-33. The regenerated transformed shoot was rooted in vitro and transferred to the greenhouse for continued growth. After two years in the greenhouse, the original greenhouse-grown plant was field planted and maintained under close observation.

The new variety was asexually propagated (originally from the greenhouse-grown plant) by bud-grafting on to standard rootstocks, including but not limited to *Prunus persica* (GF305 peach), *Prunus domestica* (European plum seedlings), *Prunus myrobalan* and [*Prunus cerasifera*×*P. munsoniana*] (GF 8-1). Comparisons of asexually propagated trees and the original plant of the new variety have shown that the characteristics of high level of PPV resistance, vigorous growth, upright tree form, productivity, high fruit quality and large fruit size are maintained. No aberrant types appeared.

The new variety serves as an effective parent for transferring the PPV coat protein gene and resistance to PPV (as described in Scorza et al. 1998. *Acta Hort.* vol. 472, pp. 421–427 and Ravelonandro et al. 1998. *Acta Hort.* vol. 478, pp. 67–71). The transgene insert is transferred as a single genetic locus and resistance acts in a dominant manner. This simply inherited dominant resistance provides resistance as described above to the major known serotypes of PPV (Ravelonandro et al. 2001. *Acta Hort.* vol. 550, pp. 431–435). The plant is not self-fertile; a pollinator is required.

Transformation of plum has been described in the literature, however trees having the characteristics as described herein have not been produced. Researchers have been unable to achieve the same combination of fruit quality, resistance to PPV, productivity and tree growth that makes the new variety commercially attractive for fruit production.

SUMMARY OF THE NEW VARIETY

The new and distinct variety of plum tree is large, productive, vigorous with an upright growth habit. The fruit is medium to large in size, is freestone with slight cling and is of excellent eating quality. The fruit has yellow flesh of firm texture and sweet flavor and blue skin. The new variety is distinguished from all other plum trees by resistance to plum pox virus infection due to the presence of the plum pox virus coat protein gene.

DETAILED DESCRIPTION OF THE NEW VARIETY

Figure 1:
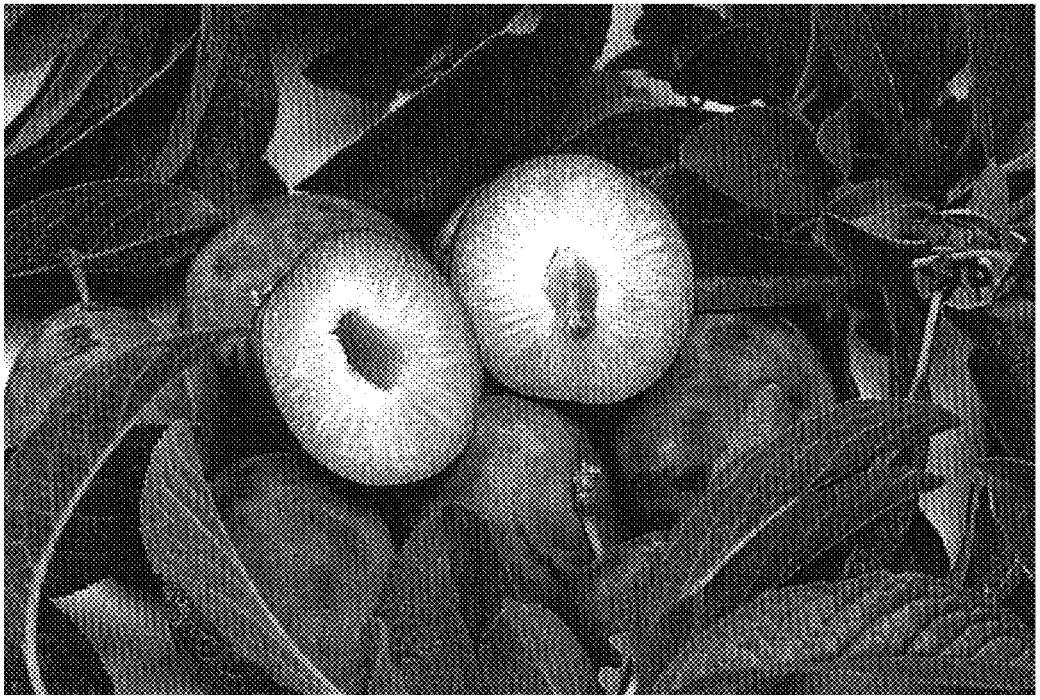
FIG. 1 is a color photograph showing fruit and leaves of the new plum variety 'HoneySweet' at maturity.
Figure 2:
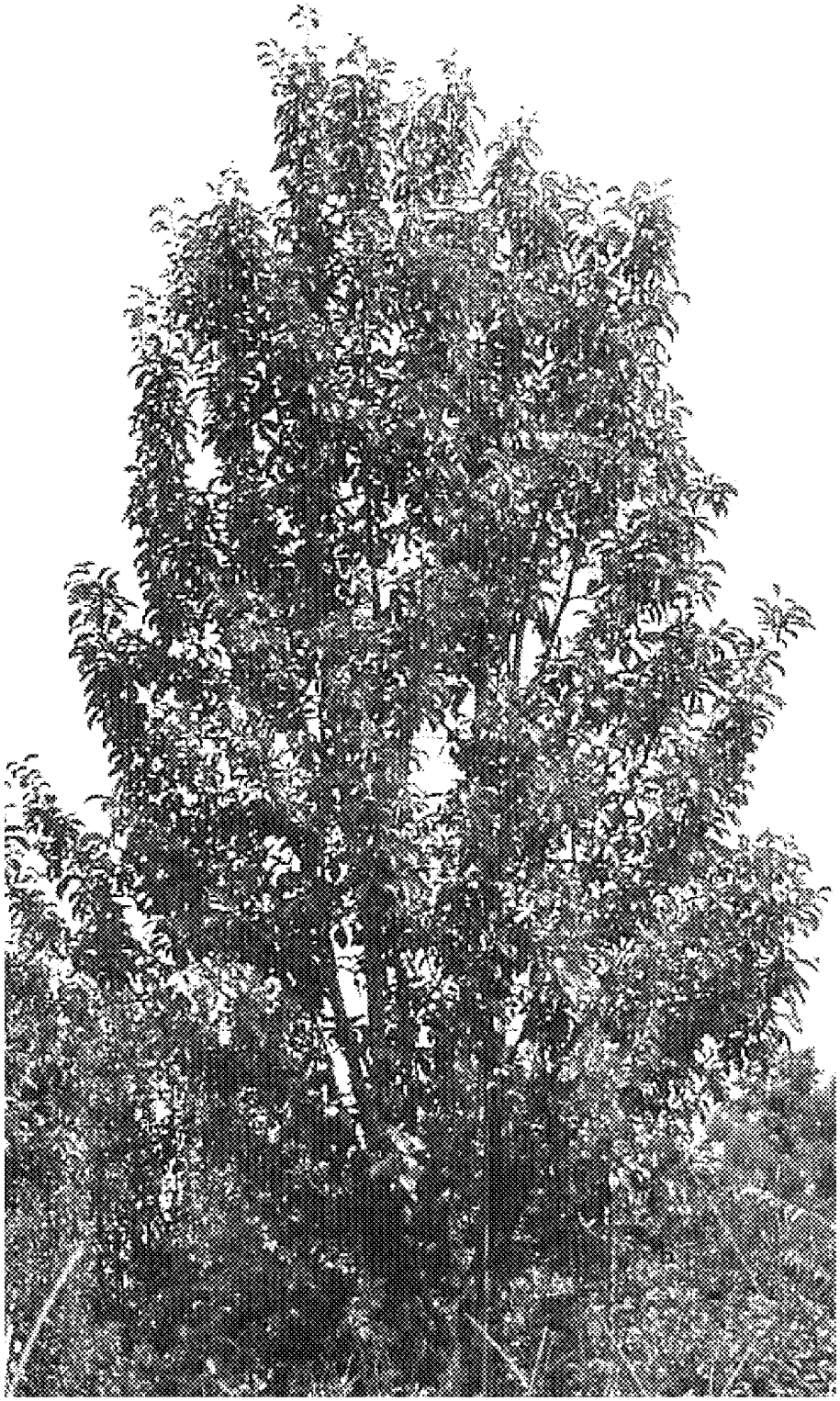
FIG. 2 is a color photograph of the tree of the new plum variety 'HoneySweet'.

The following is a detailed description of the botanical and pomological characteristics of the subject plum. Color data are presented in Royal Horticultural Society (R.H.S.) Colour Chart designations. Where dimensions, sizes, color, and other characteristics are given, it is to be understood that such characteristics are approximations of averages set forth as accurately as practicable.

The descriptions reported herein are from specimens grown at Kearneysville, W. Va.

Tree:

*Size.*—Height 4.9 m, canopy width 2.7 m at 7-yr growth in the field.

*Vigor.*—Vigorous; current season shoot length in 8-yr trees — 41.3 cm.

*Growth.*—Upright; branch angles from main limbs — 54°.

*Density.*—Medium dense to dense.

*Productivity.*—Productive; 14.4 kg/tree in 8-yr trees.

*Bearing.*—Regular; no tendency towards alternate bearing.

Trunk:

*Size.*—Moderate to large; diameter 16.5 cm at 15–20 cm above ground level; circumference 51.3 cm at 15–20 cm above ground level.

*Color.*—Ranging from RHS 197 A to D.

Branches:

*Size.*—Medium; average diameter of 1-yr branches — 3.9 mm, 2-yr branches—4.6 mm.

*Texture.*—Smooth to medium rough.

*Spur development.*—Moderate; 0.44 spurs/cm on 2-yr branches; length—5–7 mm.

*Color.*—With wax bloom, ranging from RHS 91B to 97B; with wax bloom removed, ranging from RHS 103A to RHS N186A.

*Lenticels.*—In 5–6-yr branches, 5 mm long, 2/cm$^2$; RNS 167C.

Leaves:

*Size.*—Average length 92 mm, average width 45 mm.

*Texture.*—Glabrous to somewhat rough.

*Thickness.*—Medium to thick; average thickness 0.42 mm.

*Glands.*—Two, small, round; average width 0.44 mm, length 0.52 mm; RHS 137B.

*Margin.*—Dentate.

*Form.*—Obovate-pointed.

*Petiole.*—Medium length, medium thickness with average length 11.8 mm, width 1.4 mm, thickness 1.3 mm; RHS 137B.

*Color.*—Upper (adaxial) surface — RHS 139A; lower (abaxial) surface — ranging from RHS 137 B to C.

Flowers:

*Bloom period.*—Variable depending on weather, late March to mid-April in the Eastern Panhandle of West Virginia.

*Color.*—White.

*Pollen.*—Present; RHS 11A.

*Filament.*—Average length 7.7 mm; RHS 155D.

*Pedicel.*—Average length 8.8 mm.

*Pistil.*—Average length 10.9 mm.

*Petal.*—Average size 6.9 mm×9.6 mm.

*Anther.*—RHS 13A.

*Sepal.*—RHS 143C.

*Style.*—RHS 137B.

*Description.*—Complete, perfect, perigynous; five sepals form hypanthium cup averaging 3.1 mm height and 3.7 mm diameter; 5 white petals attached to hypanthium; stamens — averaging 15/flower, attached to interior of hypanthium at or below the rim of hypanthium cup; pistil — superior, averaging 10.9 mm long; stigma—round, averaging 0.86 mm diameter; style — averaging 7.5 mm long and 0.4 mm diameter; ovary — averaging 2.5 mm height and 1.6 mm diameter; no detectable scent.

Fruit:

*Maturity when described.*—Shipping ripe-eating ripe.

*Average date of harvest.*—Mid August to early September in Kearneysville, W. Va.

*Size.*—Medium to large; average size is 43 mm transverse diameter at right angles to the suture plane×45 mm transverse diameter in the suture plane×52 mm axial diameter; average weight is 60 grams.

*Use.*—Dessert.

Flesh:

*Ripens.*—Evenly.

*Texture.*—Firm.

*Fibers.*—Small, few, tender.

*Juice.*—Moderate at eating-ripe.

*Aroma.*—Moderate.

*Flavor.*—Very good.

*Eating quality.*—Sweet, excellent; brix of ripe fruit averages 21.5° depending on maturity at harvest.

*Color.*—Ranging from RHS 6 A to C to RHS151A, depending on stage of ripeness.

*Pit cavity.*—Color same as flesh color.

Skin:

*Thickness.*—Medium.

*Tendency to crack.*—None.

*Color.*—With wax bloom, ranging from RHS 91B to 97B; with wax bloom removed ranging from RHS 103A to RHS N186A.

Stone:

*Type.*—Freestone, slight cling.

*Size.*—Medium; average length 27 mm, average width 17 mm, average thickness 10 mm.

*Form.*—Ovate/asymmetrical.

*Tendency to split.*—None.

*Color.*—RHS 165C.

*Market.*—Local and long distance for fresh markets. The plum tree and its fruit described herein may vary slightly in detail due to climate, soil conditions and cultural practices under which the variety may be grown.

We claim:

1. A new and distinct variety of plum tree, substantially as shown and described, which is large, productive, vigorous with an upright growth habit, contains the plum pox virus coat protein gene and is thereby resistant to plum pox virus infection, and produces annual crops of medium to large size, freestone fruit with yellow flesh of firm texture and sweet flavor and blue skin.

* * * * *